(12) United States Patent
Perry et al.

(10) Patent No.: US 7,652,000 B2
(45) Date of Patent: Jan. 26, 2010

(54) BORON-CONTAINING COMPOUNDS AND METHODS OF USE

(75) Inventors: David Perry, Oakland, CA (US); Kirk R. Maples, San Jose, CA (US); Carolyn Bellinger-Kawahara, Redwood City, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 255 days.

(21) Appl. No.: 11/153,765

(22) Filed: Jun. 14, 2005

(65) Prior Publication Data

US 2006/0009422 A1 Jan. 12, 2006

Related U.S. Application Data

(60) Provisional application No. 60/579,421, filed on Jun. 14, 2004.

(51) Int. Cl.
*A01N 55/08* (2006.01)
*A61K 31/435* (2006.01)

(52) U.S. Cl. ............... 514/64; 514/277; 514/859; 514/900; 514/902

(58) Field of Classification Search ............ 514/64, 514/277, 859, 900, 902
See application file for complete search history.

(56) References Cited

U.S. PATENT DOCUMENTS

| 3,780,174 A | * | 12/1973 | Hamill | ............... | 424/118 |
| 5,348,947 A | | 9/1994 | Patel | | |
| 6,123,925 A | * | 9/2000 | Barry et al. | ............... | 424/49 |
| 6,350,786 B1 | * | 2/2002 | Albano et al. | ............... | 514/772.4 |
| 2004/0224923 A1 | * | 11/2004 | Lee et al. | ............... | 514/64 |

FOREIGN PATENT DOCUMENTS

WO WO 01/35966 A1 5/2001

OTHER PUBLICATIONS

Merck Manual, Section 18, Skin Disorders (Table of Contents).*
Merck Manual, Common Dental Disorders.*
Dahlen, G., Oral Microbol. Immunol., 1995, 10, p. 42-46 (abstract).*
Mangundjaja, S., Clin. Ther., 12(3), 1990, p. 242-249.*
Shan Zixing. et al., "Synthethesis of Aromatic Nitrogen-containing Heterocyclic Derivatives of Asymmetric Diarylborinic Acids," *Journal of Wuhan University (Natural Science Edition)*, No. 3, 1990, pp. 67-72 (XP002922573).
Farfan N. et al "Boron-11 Nuclear Magnetic Rosonance Study of the Reactions of 2-Functionalized Pyridines with Borane-tetrahydrofuran and -dimethyl sulfide. Formation of Borinic esters and N → B Bond Energy Differences in Five -and Six-membered Ring Borates," *Journal of The Chemical Society, Perkin Transactions 2: Physical Organic Chemistry* (1972-1999), No. 10, 1988, pp. 1787-1791.
Nefkens G.H.L. et al., "Reactions of Boroxazolidones with Aromatic Aldehydes. An Easy Route to Derivatives of Isoquinoline and Isoindolinone," *Tetrahedron*, vol. 41, No. 24, 1985, pp. 6063-6066.
Lin Kai, et al., "Synthesis and Antitumor Activity of Organyloxy-diarylborane Chelates Containing A Quinoline Ring," *Yiyago Gongye (Pharmaceutical Industy)*, vol. 16, No. 11, 1985, pp. 500-502 (XP009057311).
Hohaus E. et al., "Mass Spectometric Studies of Boron Chelates of the Pyridine and Quinoline Series and their N-Oxides," *Zeitschrift Fuer Naturforschung, Teil B: Anorganische Chemie, Organische Chemie, Biochemie, Biophysik, Biologie*, vol. 28, Nos. 7-8, 1973, pp. 440-445 (XP008006864).
Hohaus E. et al., "Boron Chelates and Boron Metal Chelates. I. Boron Chelates with Chelating Agents of the Pyridine and Quinoline Series and their N-Oxides," *Chemische Berichte*, vol. 102, No. 12, 1969, pp. 4025-4031 (XP-002127342).
Jianming, L. et al., "Synthesis of 3,4<-Dichlorofuran Derivatives and Their Biological Activities," *Pharmaceutical Insustry*, 1985, pp. 16-21.

* cited by examiner

*Primary Examiner*—Michael G Hartley
*Assistant Examiner*—Leah Schlientz
(74) *Attorney, Agent, or Firm*—Morgan, Lewis & Bockius, LLP

(57) ABSTRACT

Methods of treating and/or preventing surface infections, such as acne, in an animal, such as a human being, using antibiotics incorporating borinic acid complexes, especially picolinic acid derivatives, are disclosed, along with compositions of these antibiotics.

32 Claims, No Drawings

BORON-CONTAINING COMPOUNDS AND METHODS OF USE

1 CROSS REFERENCE TO RELATED U.S. PATENT APPLICATIONS

This application claims the benefit under 35 U.S.C. § 119(e) of provisional U.S. Patent Application Ser. No. 60/579,421, filed Jun. 14, 2004. The contents of this application are incorporated herein in their entirety and for all purposes.

2 BACKGROUND OF THE INVENTION

2.1 Field of the Invention

The present invention relates to the field of boron-containing compounds, particularly compounds with antibacterial, anti-inflammatory, or both activities, and uses thereof. Methods for preparing and using these antibiotics, and pharmaceutical compositions thereof, are also provided.

2.2 The Related Art

Acne vulgaris is the most common skin disease which affects 85% of individuals at some time between the ages of 12- and 24 years. At present, 45 million people in the US have acne, while 17 million Americans seek treatment every year. Acne is a disease of the pilosebaceous unit, involving abnormalities in sebum production, follicular epithelial desquamation, bacterial proliferation and inflammation. The pathogenesis of acne is multifactorial, with microbial proliferation and inflammation acting as central mediators to this condition. In hair follicles, the mixture of cells and sebum creates an environment for the proliferation of *Propionibacterium acnes* (*P. acnes*), a bacterium that occurs commonly on the skin. Chemotactic factors released by *P. acnes* attract lymphocytes and neutrophils, as well as producing other pro-inflammatory molecules. This results in an inflammatory process where a plug composed of skin cells and sebum in sebaceous follicles is formed.

Current treatments for acne include antibiotics applied topically and systemically and also topical retinoids. However, these treatments are not satisfactory due to the long time course of therapy, which usually can take four to six weeks or longer. In addition, topical irritation and systemic side effects are also major issues with current products. Therefore, there is a need for an improved therapy for acne that is shorter acting, devoid of side effects, and inhibits both the bacterial and inflammatory contributors to the pathogenesis. The present invention addresses these problems by providing borinic esters that exhibit anti-inflammatory and/or antibacterial activities. Thus, the present invention represents a new modality for the treatment of acne.

Rosacea is a chronic skin disease that causes redness and swelling, mostly of the face and eyes. It is sometimes referred to as "adult acne". The cause of rosacea is unknown and may be inherited. The disease affects 14 million Americans, occurs mostly in adults, is more common in women but is more severe in men. The current treatments are quite ineffective and may take weeks to months to see only a slight improvement. Thus, new therapies for rosacea are badly needed.

Acne and rosacea are common conditions that have a concomitant inflammatory component to their pathology. Inflammation is a defense reaction caused by tissue damage or injury, characterized by redness, heat, swelling, and pain. The primary objective of inflammation is to localize and eradicate the irritant and repair the surrounding tissue. For the survival of the host, inflammation is a necessary and beneficial process. The inflammatory response involves three major stages: first, dilation of capillaries to increase blood flow; second, microvascular structural changes and escape of plasma proteins from the bloodstream; and third, leukocyte transmigration through endothelium and accumulation at the site of injury. The leukocyte adhesion cascade is a sequence of adhesion and activation events that ends with extravasation of the leukocyte, whereby the cell exerts its effects on the inflamed site. These steps are not phases of inflammation, but represent the sequence of events from the perspective of each leukocyte. One goal of inflammation research is to develop methods to control inflammation by modulating or blocking leukocyte adhesion to the endothelium. This can result in the discovery of new anti-inflammatory agents. Anti-inflammatory agents function as blockers, suppressors, or modulators of the inflammatory response. The inflammatory response begins with a release of inflammatory chemicals into the extracellular fluid. Sources of these inflammatory mediators, the most important of which are histamine, prostaglandins, and cytokines, are injured tissue cells, lymphocytes, mast cells and blood proteins. The presence of these chemicals promotes and furthers the reactions to inflammation, which are redness, heat, swelling, and pain.

Anti-inflammatory drugs block or suppress the inflammatory response, preventing or reducing the appearance of adverse reactions to the irritant. Diseases and conditions such as acne, rosacea, asthma, arthritis, psoriasis and atopic dermatitis, for example, are treated with non-steroidal or steroidal anti-inflammatory agents. Aspirin and some other anti-inflammatory drugs exert their analgesic effects by inhibiting prostaglandin synthesis. In one aspect, the present invention relates to borinic esters that demonstrate anti-inflammatory activity by blocking the production of pro-inflammatory cytokines. These cytokines include, but are not limited to IL-1β, TNF-α, IL-6 and IL-8. The action of blocking these cytokines with compounds disclosed herein results in a reduction in the inflammatory components of redness, heat, swelling and pain.

While such treatments have historically required protracted therapeutic modalities, some drugs are not esthetically acceptable (often resulting in intense reddening, peeling, or drug coloration) which detract from patient adherence to the treatments. The products described herein are typically white colored and have enhanced stability. Thus, the present invention addresses a number of vexing diseases.

3 SUMMARY OF THE INVENTION

In one aspect, the present invention relates to methods of using compounds having anti-inflammatory and/or anti-bacterial activity. The compounds useful in the methods of the invention are borinate derivatives, especially borinic acid complexes with picolinic acids.

In one embodiment, the compounds useful in the methods of the invention are also provided as pharmaceutical compositions that can be administered to an animal, most preferably a human, for treatment of a disease having a bacterial etiology, or an topical opportunistic infection with a bacteria in an animal, most preferably a human, in an immunologically compromised or debilitated state of health.

In preferred embodiments, the compounds useful in the methods of the invention are those having the structures given by Formula 2 below and elsewhere, with preferred substituents as disclosed herein.

The invention also provides methods for preparing the compounds and pharmaceutical compositions thereof, and methods of using said compounds therapeutically. Kits and packaged embodiments of the compounds and pharmaceutical compositions of the invention are also contemplated.

The invention also relates to methods of treating infections, preferably bacterial infections, using the compounds disclosed herein.

These and other aspects and advantages will become apparent in the Description below.

4 DESCRIPTION OF SOME EMBODIMENTS OF THE INVENTION

This invention provides methods of using compounds, specifically the antibacterial and/or anti-inflammatory compounds disclosed herein, for treating and/or preventing bacterial infections, especially skin conditions, such as skin irritations and other conditions characterized by inflammation, especially localized inflammation, most preferably acne and rosacea.

The invention provides methods of treating skin conditions using a compound having the structure shown below (Formula 1):

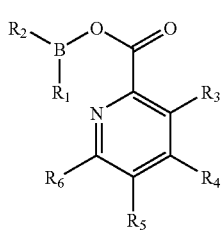

Formula 1 wherein B is boron and O is oxygen; $R_1$ and $R_2$ are selected independently from the group consisting of optionally substituted alkyl, optionally substituted aryl, aralkyl, and optionally substituted heteroaryl. $R_3$ and $R_4$ are selected from the group consisting of: hydrogen, alkyl, aryl, aralkyl, heteroaryl, heteroaralkyl, cycloalkyl, heterocyclyl, —C(O)-aryl, —OC(O)-alkyl, —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NHalkyl, —CH$_2$N(alkyl)$_2$, —CO$_2$H, —CO$_2$alkyl, —CONH$_2$, —OH, alkoxy, aryloxy, —SH, —S-alkyl, —S-aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, and —CONHalkyl. The alkyl, aryl, aralkyl, heteroaryl, heteroaralkyl, cycloalkyl and heterocyclic groups in all of the $R_3$ and $R_4$ substituents are optionally substituted. $R_5$ and $R_6$ are selected independently from the group consisting of: hydrogen, alkyl, aryl, aralkyl, heteroaryl, heteroaralkyl, cycloalkyl, heterocyclyl, —(CH$_2$)$_n$OH (n=1 to 3), —CH$_2$NH$_2$, —CH$_2$NHalkyl, —CH$_2$N(alkyl)$_2$, halogen, —CHO, —CH=NOH, —CO$_2$H, —CO$_2$-alkyl, —S-alkyl, —SO$_2$-alkyl, —SO-alkyl, —S-aryl, —SO$_2$N(alkyl)$_2$, —SO$_2$NHalkyl, —SO$_2$NH$_2$, —NH$_2$, alkoxy, —CF$_3$, —SCF$_3$, —NO$_2$, —SO$_3$H, and —OH; wherein alkyl, aryl, aralkyl, heteroaryl, heteroaralkyl, cycloalkyl and heterocyclic groups in all of the $R_5$ and $R_6$ substituents are optionally substituted and further wherein $R_5$ and $R_6$ together with the ring to which they are attached form an optionally substituted aromatic ring or its pharmaceutically acceptable salts, hydrates, or solvates.

In some embodiments of the method of the invention, the compounds of Formula 1 include those for which one of $R_1$ and $R_2$ is optionally substituted aryl. In more specific embodiments for which one of $R_1$ and $R_2$ is optionally substituted aryl, one of $R_1$ and $R_2$ is optionally substituted heteroaryl to provide thereby mixed aryl-heteroaryl substituents. In a still more specific embodiment in which one of $R_1$ and $R_2$ is optionally substituted aryl and one of $R_1$ and $R_2$ is optionally substituted heteroaryl, the optionally substituted heteroaryl is optionally substituted pyridyl. Yet more specific embodiments for which one $R_1$ and $R_2$ is optionally substituted pyridyl include those for which one of $R_1$ and $R_2$ is optionally substituted phenyl. In more specific embodiments, the optionally substituted phenyl is phenyl substituted by a moiety selected from the group consisting of alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, —S-alkyl, —S-aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl.

In other embodiments of the invention, the compounds of Formula 1 include those in which both $R_1$ and $R_2$ are optionally substituted aryl. More particular embodiments for which both $R_1$ and $R_2$ are optionally substituted aryl are those where each of $R_1$ and $R_2$ is optionally substituted phenyl. Still more specific embodiments for which each of $R_1$ and $R_2$ is optionally substituted phenyl are those wherein $R_3$ is H, —OH, alkoxy, or carboxy. Among these embodiments are compounds in which the optionally substituted phenyl is phenyl substituted by a moiety selected from the group consisting of alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, S-alkyl, S-aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl. In yet more particular embodiments of those just described, $R_3$ is —OH or carboxy. Specific embodiments are provided in the examples below.

In still other embodiments of the invention, each of $R_1$ and $R_2$ is optionally substituted phenyl and the optionally substituted phenyl is substituted by a moiety selected from the group consisting of alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, —S-alkyl, —S-aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl and $R_3$ is —OH. More particular embodiments of these compounds include those in which the optionally substituted phenyl is phenyl substituted by a moiety selected from the group consisting of: hydrogen, halogen, and alkyl, and, more particularly, those wherein the halogen is chloro, still more particularly, those wherein the halogen is chloro and the alkyl is methyl. A particularly useful compound among the latter embodiments is (bis(3-chloro-4-methylphenyl)boryloxy)(3-hydroxypyridin-2-yl)methanone, including its pharmaceutically acceptable salts, solvates, and hydrates.

In another aspect, the invention provides methods for treating a skin condition (including topical skin disorders such as acne and atopic dermatitis, and tissue conditions such as disorders of mucosal tissues (e.g., periodontal diseases), and systemic inflammatory tissue disorders such as arthritis) using the compounds described herein. In one embodiment, the skin condition is an inflammation of the skin. More particularly, the compounds described herein can be useful where the skin condition is selected from the group consisting of: acne vulgaris, acne rosacea, psoriasis, periodontal disease, arthritis, and atopic dermatitis. Particular embodiments include those wherein the skin condition is acne vulgaris. In another embodiment, the skin condition is acne rosacea. Still other particular skin conditions include psoriasis and atopic dermatitis.

In yet another aspect, the present invention provides methods for inhibiting the release of a pro-inflammatory cytokine in an animal by administering an inhibitory amount of a compound of Formula 1 to the animal in need. In some embodiments of the invention, the pro-inflammatory cytokine is selected from the group consisting of IL-1α, TNF-α, and IL-6. Some particular embodiments include those compounds of Formula 1 for which each of $R_1$ and $R_2$ is optionally substituted phenyl, the optionally substituted phenyl is phenyl substituted by a moiety selected from the group consisting of: hydrogen, alkyl, cycloalkyl, aryl, substituted aryl, aralkyl, —$(CH_2)_k$OH (where k=1, 2 or 3), —$CH_2NH_2$, —$CH_2NH$-alkyl, —$CH_2N(alkyl)_2$, —$CO_2H$, —$CO_2$alkyl, —$CONH_2$, —CONHalkyl, —$CON(alkyl)_2$, —OH, alkoxy, aryloxy, —SH, —S-alkyl, —S-aryl, —$SO_2$alkyl, —$SO_2N(alkyl)_2$, —$SO_2$NHalkyl, —$SO_2NH_2$, —$SO_3H$, —$SCF_3$, —CN, halogen, —$CF_3$, —$NO_2$, amino, substituted amino, —$NHSO_2$alkyl, —$OCH_2CH_2NH_2$, —$OCH_2CH_2$NHalkyl, —$OCH_2CH_2N(alkyl)_2$, oxazolidin-2-yl, and alkyl substituted oxazolidin-2-yl and $R_3$ is —OH.

In another aspect, the invention provides methods of using compounds having the structure of Formula 2:

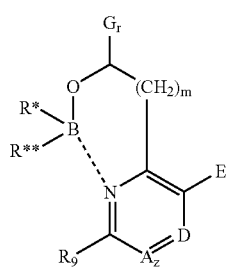

Formula 2 including its salts, solvates, and hydrates, wherein B is boron, O is oxygen; and wherein R* and R** are each independently selected from optionally substituted alkyl ($C_1$-$C_6$), optionally substituted cycloalkyl ($C_3$-$C_7$), optionally substituted alkenyl, optionally substituted alkynyl, aralkyl, optionally substituted phenyl, and optionally substituted heterocycle; and wherein z is zero or one and when z is one, A is CH, $CR^{10}$ or N, and wherein D is N, CH, or $CR^{12}$; and wherein E is H, OH, alkoxy or 2-(morpholino)ethoxy, —$CO_2H$ or $CO_2$alkyl; and wherein m=0-2.

The variable r is 1 or 2. When r is 1, G is =O (double-bonded oxygen), and when r is 2 each G is independently hydrogen, methyl, ethyl or propyl. $R^{12}$ is selected from —$(CH_2)_k$OH (where k=1, 2 or 3), —$CH_2NH_2$, —$CH_2NH$-alkyl, —$CH_2N(alkyl)_2$, —$CO_2H$, —$CO_2$alkyl, —OH, alkoxy, aryloxy, —SH, —S-alkyl, —S-aryl, —$SO_2$alkyl, —$SO_2N(alkyl)_2$, —$SO_2$NHalkyl, —$SO_2NH_2$, —$SO_3H$, —$SCF_3$, —CN, halogen, —$CF_3$, —$NO_2$, amino, substituted amino, —$NHSO_2$alkyl and —$CONH_2$; and wherein $R^9$ and $R^{10}$ are each independently selected from the group consisting of hydrogen, alkyl, cycloalkyl, —$(CH_2)_n$OH (n=1 to 3), —$CH_2NH_2$, —$CH_2$NHalkyl, —$CH_2N(alkyl)_2$, halogen, —CHO, —CH=NOH, —$CO_2H$, —$CO_2$-alkyl, —S-alkyl, —$SO_2$-alkyl, —S-aryl, —$SO_2N(alkyl)_2$, —$SO_2$NHalkyl, —$SO_2NH_2$, alkoxy, —$CF_3$, —$SCF_3$, —$NO_2$, —$SO_3H$ and —OH.

In a preferred embodiment, the methods of the invention utilize compounds of Formula 2 wherein R* and R** are the same or are different and wherein one of R* and R** is an optionally substituted alkyl ($C_1$-$C_6$) or R* and R** are each an optionally substituted alkyl ($C_1$-$C_6$).

In another preferred embodiment, the methods of the invention utilize compounds of Formula 2 wherein R* and R** are the same or are different and wherein one of R* and R** is an optionally substituted cycloalkyl ($C_3$-$C_7$) or R* and R** are each an optionally substituted cycloalkyl ($C_3$-$C_7$).

In yet another preferred embodiment, the methods of the invention utilize compounds of Formula 2 wherein R* and R** are the same or are different and wherein one of R* and R** is an optionally substituted alkenyl or R* and R** are each an optionally substituted alkenyl. In a further preferred embodiment thereof, the alkenyl is a substituted vinyl having the following structure:

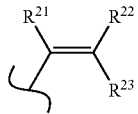

wherein $R^{21}$, $R^{22}$, and $R^{23}$ are each independently selected from the group consisting of hydrogen, alkyl, aryl, cycloalkyl, substituted aryl, aralkyl, —$(CH_2)_k$OH (where k=1, 2 or 3), —$CH_2NH_2$, —$CH_2NH$-alkyl, —$CH_2N(alkyl)_2$, —$CO_2H$, —$CO_2$alkyl, —$CONH_2$, —S-alkyl, —S-aryl, —$SO_2$alkyl, —$SO_2N(alkyl)_2$, —$SO_2$NHalkyl, —$SO_2NH_2$, —$SO_3H$, —$SCF_3$, —CN, halogen, —$CF_3$ and —$NO_2$.

In a preferred embodiment the methods of the invention utilize compounds of Formula 2 wherein R* and R** are the same or are different and wherein one of R* and R** is an optionally substituted alkynyl or R* and R** are each an optionally substituted alkynyl. In a further preferred embodiment thereof, the alkynyl has the structure:

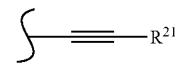

wherein $R^{21}$ is selected from the group consisting of hydrogen, alkyl, cycloalkyl, aryl, substituted aryl, aralkyl, —$(CH_2)_k$OH (where k=1, 2 or 3), —$CH_2NH_2$, —$CH_2NH$-alkyl, —$CH_2N(alkyl)_2$, —$CO_2H$, —$CO_2$alkyl, —$CONH_2$-alkyl, —S-alkyl, —S-aryl, —$SO_2$alkyl, —$SO_2N(alkyl)_2$, —$SO_2$NHalkyl, —$SO_3H$, —$SCF_3$, —CN, halogen, —$CF_3$ and —$NO_2$.

In a preferred embodiment the methods of the invention utilize compounds of Formula 2 wherein R* and R** are the same or are different and wherein one of R* and R** is an optionally substituted phenyl or R* and R** are each an optionally substituted phenyl excluding combinations of Formula 2 wherein z is 1, A is $CR^{10}$, D is $CR^{12}$, J is $CR^{10}$ and excluding combinations of Formula 2 wherein z is 1, A is $CR^{10}$, D is $CR^2$, m is 2, G is H or methyl or ethyl, or propyl.

A preferred embodiment involves use of a compound of Formula 2 wherein R* and R** are each other than an optionally substituted phenyl.

Another preferred embodiment involves use of a compound of Formula 2 wherein one of R* or R** is an optionally substituted benzyl.

An additional preferred embodiment involves use of a compound of Formula 2 wherein r is 1, G is =O, m is zero and E is OH.

A preferred embodiment involves use of a compound of Formula 2 wherein z is 1 and $R^9$ is selected from alkyl (greater than $C_4$), —$(CH_2)_n$OH (n=1, 2 or 3), —$CH_2NH_2$, —$CH_2$NHalkyl, —$CH_2$N(alkyl)$_2$, —CHO, —CH=NOH, —$CO_2$H, —$CO_2$-alkyl, —S-alkyl, —$SO_2$-alkyl, —S-aryl, alkoxy (greater than $C_4$), —$SCF_3$, and —$NO_2$.

In one preferred embodiment, the compound used has the structure of Formula 2 wherein z is 1 and $R^{10}$ is selected from alkyl (greater than $C_4$), —$(CH_2)_n$OH (n=1, 2 or 3), $CH_2NH_2$, —$CH_2$NHalkyl, —$CH_2$N(alkyl)$_2$, —CHO, —CH=NOH, —$CO_2$H, —$CO_2$-alkyl, —S-alkyl, —$SO_2$-alkyl, —S-aryl, alkoxy (greater than $C_4$), —$SCF_3$, and —$NO_2$.

In another preferred embodiment, the compound used has the structure of Formula 2 wherein z is 1 and D is $CR^{12}$ wherein $R^{12}$ is selected from —$(CH_2)_k$OH (where k=1, 2 or 3), —$CH_2SO_2$alkyl, —$CH_2$NH-alkyl, —$CH_2$N(alkyl)$_2$, —$CO_2$H, —$CO_2$alkyl, —$CONH_2$, —OH, alkoxy (greater than C4), aryloxy, —SH, —S-alkyl, —S-aryl, —$SO_2$alkyl, —$SO_3$H, —$SCF_3$, —CN, —$NO_2$, —$NH_2SO_2$alkyl, and $CONH_2$.

In an additional preferred embodiment the compound used has the structure of Formula 2 wherein z is 1, E is N-(morpholinyl)ethoxy or alkoxy greater than $C_4$.

Other preferred embodiments utilize compounds having the structure of Formula 2 wherein A or D is nitrogen, or wherein m is 2.

In another preferred embodiment, the compound used has the structure of Formula 2 wherein one of R* or R** is substituted phenyl substituted with 1 to 5 substituents each of which is independently selected from alkyl (greater than $C_6$), aryl, substituted aryl, benzyl, substituted benzyl, —$(CH_2)_k$OH (where k=1, 2 or 3), —$CH_2NH_2$-alkyl, —$CH_2$NH-alkyl, —$CH_2$N(alkyl)$_2$, —$CO_2$H, —$CO_2$alkyl, —$CONH_2$, —CONHalkyl, —CON(alkyl)$_2$, —OH, alkoxy (greater than $C_6$), aryloxy, —SH, —S-alkyl, —S-aryl, —$SO_2$alkyl, —$SO_3$H, —$SCF_3$, —CN, —$NO_2$, amino, substituted amino, —$NHSO_2$-alkyl, —$OCH_2CH_2NH_2$, —$OCH_2CH_2$NHalkyl, —$OCH_2CH_2$N(alkyl)$_2$, oxazolidin-2-yl, and alkyl-substituted oxazolidin-2-yl.

In a further preferred embodiment thereof, the phenyl has the structure:

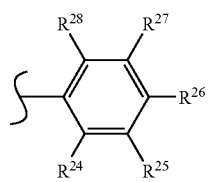

wherein $R^{24}$, $R^{25}$, $R^{26}$, $R^{27}$ and $R^{28}$ are each independently selected from the group consisting of hydrogen, alkyl, cycloalkyl, aryl, substituted aryl, aralkyl, —$(CH_2)_k$OH (where k=1, 2 or 3), —$CH_2NH_2$, —$CH_2$NH-alkyl, —$CH_2$N(alkyl)$_2$, —$CO_2$H, —$CO_2$alkyl, —$CONH_2$, —CONHalkyl, —CON(alkyl)$_2$, —OH, alkoxy, aryloxy, —SH, —S-alkyl, —S-aryl, —$SO_2$alkyl, —$SO_2$N(alkyl)$_2$, —$SO_2$NHalkyl, —$SO_2NH_2$, —$SO_3$H, —$SCF_3$, —CN, halogen, —$CF_3$, —$NO_2$, amino, substituted amino, —$NHSO_2$-alkyl, —$OCH_2CH_2NH_2$, —$OCH_2CH_2$NHalkyl, —$OCH_2CH_2$N(alkyl)$_2$, oxazolidin-2-yl, or alkyl substituted oxazolidin-2-yl.

In a very preferred embodiment, the present invention provides methods that utilize a compound of Formula 2 wherein R* is the same as R** which is 3-chloro-4-methylphenyl, $R^9$ is hydrogen, $R^{11}$ is hydrogen, A is CH, D is CH and E is —OH, m=zero, r is 1, G is =O (double bonded oxygen) and is named bis(3-chloro-4-methylphenyl)borinic acid 3-hydroxypicolinate ester.

In a very preferred embodiment, the present invention provides methods that utilize a compound of formula 2 wherein R* is the same as R** which is 2-methyl-4-chlorophenyl, $R^9$ is hydrogen, $R^{11}$ is hydrogen, A is CH, D is CH and E is —OH, m=zero, r is 1, G is =O (double bonded oxygen) and is named bis(2-methyl-4-chlorophenyl)borinic acid 3-hydroxypicolinate ester.

In a preferred embodiment the methods of the invention utilize compounds of Formula 2 wherein R* and R** are the same or are different and wherein one of R* and R** is an optionally substituted benzyl or R* and R** are each an optionally substituted benzyl. In a further preferred embodiment thereof, the benzyl has the structure:

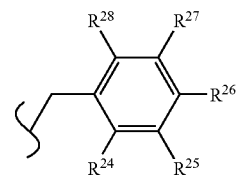

wherein $R^{24}$, $R^{25}$, $R^{26}$, $R^{27}$ and $R^{28}$ are each independently selected from the group consisting of hydrogen, alkyl, cycloalkyl, aryl, substituted aryl, aralkyl, —$(CH_2)_k$OH (where k=1, 2 or 3), $CH_2NH_2$, —$CH_2$NH-alkyl, —$CH_2$N(alkyl)$_2$, —$CO_2$H, —$CO_2$alkyl, —$CONH_2$l, —CONHalkyl, —CON(alkyl)$_2$, —OH, alkoxy, aryloxy, —SH, —S-alkyl, —S-aryl, —$SO_2$alkyl, —$SO_2$N(alkyl)$_2$, —$SO_2$NHalkyl, —$SO_2NH_2$, —$SO_3$H, —$SCF_3$, —CN, halogen, —$CF_3$, —$NO_2$, amino, substituted amino, —$NHSO_2$alkyl, —$OCH_2CH_2NH_2$, —$OCH_2CH_2$NHalkyl, —$OCH_2CH_2$N(alkyl)$_2$, oxazolidin-2-yl, or alkyl substituted oxazolidin-2-yl.

In a preferred embodiment the methods of the invention utilize compounds of Formula 2 wherein R* and R** are the same or are different and wherein one of R* and R** is an optionally substituted heteroaryl or R* and R** are each an optionally substituted heteroaryl. In a further preferred embodiment thereof, the optionally substituted heteroaryl has the structure:

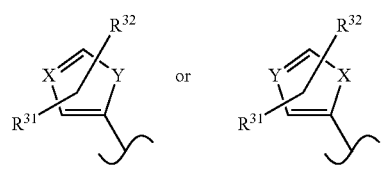

wherein X is CH=CH, N=CH, NR³³ (wherein R³³=H, alkyl, aryl or aralkyl), O, or S;

and wherein Y is CH or N when X is O, N or S;

and wherein R³¹ and R³² are each independently selected from the group consisting of hydrogen, alkyl, cycloalkyl, aryl, substituted aryl, aralkyl, —(CH₂)ₖOH (where k=1, 2 or 3), —CH₂NH₂, —CH₂NH-alkyl, —CH₂N(alkyl)₂, —CO₂H, —CO₂alkyl, —CONH₂, —S-alkyl, —S-aryl, —SO₂alkyl, —SO₂N(alkyl)₂, —SO₂NHalkyl, —NHSO₂-alkyl, —SO₃H, —SCF₃, —CN, halogen, —CF₃, —NO₂, oxazolidin-2-yl, or alkyl substituted oxazolidin-2-yl.

In a preferred embodiment, the invention provides a method of using a compound of Formula 2 wherein R⁹ is hydrogen, R¹¹ is hydrogen A is CH, D is CH, J is CH. In a preferred embodiment, the invention provides a method of using a compound of Formula 2 wherein R⁹ is hydrogen, R¹¹ is hydrogen, A is CH, D is CH and E is —OH, m=zero, r is 1, G is ═O (double bonded oxygen).

The structures of compounds useful in any of the methods of the invention also permit solvent interactions that may afford structures (such as Formula 3) that include atoms derived from the solvent encountered by the compounds of the invention during synthetic procedures and therapeutic uses. Thus, such solvent structures can especially insinuate themselves into at least some of the compounds of the invention, especially between the boron and nitrogen atoms, to increase the ring size of such compounds by one or two atoms. For example, where the boron ring of a structure of the invention comprises 5 atoms, including, for example, the boron, a nitrogen, an oxygen and 2 carbons, insinuation of a solvent between the boron and nitrogen would afford a 7-membered ring. In one example, use of hydroxyl and amino solvents may afford structures containing an oxygen or nitrogen between the ring boron and nitrogen atoms to increase the size of the ring. Such structures are expressly contemplated by the present invention, preferably where R*** is H or alkyl.

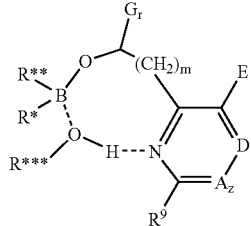

Formula 3

As used herein, the following terms have the stated meaning unless specifically defined otherwise in this application:

By "alkyl" in the present invention is meant straight or branched chain alkyl groups having 1-10 carbon atoms and preferably 1-6 carbon atoms. The terms "lower alkyl", and "C₁-C₆ alkyl" both refer to alkyl groups of 1-6 carbon atoms. Examples of such alkyl groups include, for instance, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "substituted alkyl" is meant an alkyl group having from 1 to 5 and preferably 1 to 3 and more preferably 1 substituent selected from alkoxy, substituted alkoxy, aryl, substituted aryl, aryloxy, substituted aryloxy, cycloalkyl, substituted cycloalkyl, heteroaryl, substituted heteroaryl, heterocyclic, substituted heterocyclic, hydroxyl, amino, substituted amino, carboxyl, -carboxyl-alkyl, amido, thiol, thioalkyl, substituted alkylthio, arylthio, substituted arylthio, —SO₂-alkyl, —SO₂-amino, —SO₂-substituted amino, —SO₂—OH, —SCF₃, cyano, halo, nitro, and —NHSO₂alkyl.

By "substituted lower alkyl" is meant a lower alkyl group substituted with 1 to 5 and preferably 1 to 3 and more preferably 1 substituent as defined above for substituted alkyl.

By "alkylene" is meant a divalent alkyl group having from 1 to 10 carbon atoms, preferably from 1 to 5 carbon atoms and more preferably 1 to 3 carbon atoms. This term is exemplified by groups such as methylene, 1,2-ethylene, 1,3-n-propylene, 1,4-n-butylene, 2-methyl-1,4-propylene and the like.

By "substituted alkylene" is meant an alkylene group having from 1 to 5 and preferably 1 to 3 and more preferably 1 substituent as defined above for substituted alkyl.

By "alkoxy", "lower alkoxy", and "C₁-C₆ alkoxy" is meant straight or branched chain alkoxy groups having 1-6 carbon atoms, such as, for example, methoxy, ethoxy, propoxy, isopropoxy, n-butoxy, sec-butoxy, tent butoxy, pentoxy, 2-pentyl, isopentoxy, neopentoxy, hexoxy, 2-hexoxy, 3-hexoxy, and 3-methylpentoxy.

By "substituted alkoxy" is meant —O-substituted alkyl.

By "substituted lower alkoxy" is meant a —O-lower alkyl group substituted with 1 to 5 and preferably 1 to 3 and more preferably 1 substituent as defined above for substituted alkyl.

By "alkenyl" in the present invention is meant an alkenyl group having from 2 to 6 carbon atoms and more preferably 2 to 4 carbon atoms and having at least 1 and preferably 1 site of alkenyl unsaturation. Examples of alkenyl groups include, for instance, vinyl, allyl, n-but-2-en-1-yl, and the like.

By "substituted alkenyl" is meant an alkenyl group having from 1 to 3 substituents and preferably one substituent selected from alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, thioalkyl, substituted alkylthio, arylthio, substituted arylthio, —SO₂-alkyl, —SO₂-amino, —SO₂-substituted amino, —SO₂—OH, —SCF₃, cyano, halo, nitro, —NHSO₂alkyl, and —C(O)SO₂-alkyl with the proviso that any hydroxyl or thiol substitution is not on a vinyl carbon atom.

The terms alkenyl and substituted alkenyl encompass both the cis and trans isomers as well as mixtures thereof.

By "alkynyl" is meant an alkynyl group having from 2 to 6 carbon atoms and more preferably 2 to 4 carbon atoms and having at least 1 and preferably 1 site of alkynyl unsaturation. Examples of alkynyl groups include, for instance, acetylenyl, propargyl, n-but-2-yn-1-yl, and the like.

By "substituted alkynyl" is meant an alkynyl group having from 1 to 3 substituents and preferably one substituent selected from alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, thioalkyl, substituted alkylthio, arylthio, substituted arylthio, —SO₂-alkyl, —SO₂-amino, —SO₂-substituted amino, —SO₂—OH, —SCF₃, cyano, halo, nitro, —NHSO₂alkyl, and —C(O)SO₂-alkyl with the proviso that any hydroxyl or thiol substitution is not on an acetylenic carbon atom.

By "amino" is meant —NH₂.

By "substituted amino" is meant as an —NR'R" group where R' and R" are independently selected from hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic or where R' and R" and the nitrogen atom bound thereto form a heterocyclic or substituted heterocyclic group with the proviso that R' and R" and not both hydrogen.

By "acyloxy" is meant the groups —OC(O)alkyl, —O(C) substituted alkyl, —OC(O)alkenyl, —OC(O)substituted alkenyl, —OC(O)alkynyl, —OC(O)substituted alkynyl, —OC(O)aryl, —OC(O)substituted aryl, —OC(O)cycloalkyl, —O(CO)substituted cycloalkyl, —OC(O)heteroaryl, —OC(O)substituted heteroaryl, —OC(O)heterocyclic, and —OC(O)substituted heterocyclic.

By "lower acyloxy" is meant —OC(O)-lower alkyl, whereby lower alkyl is defined above.

By "amido" is meant —C(O)amino and —C(O)substituted amino.

By the term "halogen" or "halo" is meant fluorine, bromine, chlorine, and iodine.

By "cycloalkyl", e.g., $C_3$-$C_7$ cycloalkyl, is meant cycloalkyl groups having 3-7 atoms such as, for example cyclopropyl, cyclobutyl, cyclopentyl, cyclohexyl, and cycloheptyl.

By "substituted cycloalkyl" is meant a cycloalkyl group having from 1 to 3 and preferably one substituent selected from alkyl, substituted alkyl, alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, thioalkyl, substituted alkylthio, arylthio, substituted arylthio, —$SO_2$-alkyl, —$SO_2$-amino, —$SO_2$-substituted amino, —$SO_2$—OH, —$SCF_3$, cyano, halo, nitro, —$NHSO_2$alkyl, —C(O)$SO_2$-alkyl, keto (C=O) and thioketo (C=S).

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), provided that the point of attachment is to an aromatic carbon atom.

By "substituted aryl" is meant an aryl group having from 1 to 3 and preferably one substituent selected from acyloxy, alkyl, substituted alkyl, alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, thioalkyl, substituted alkylthio, arylthio, substituted arylthio, —$SO_2$-alkyl, —$SO_2$-amino, —$SO_2$-substituted amino, —$SO_2$—OH, —$SCF_3$, cyano, halo, nitro, —$NHSO_2$alkyl, and —C(O)$SO_2$-alkyl. In one embodiment, the substituted aryl group is mono-, di-, or tri-substituted with halo, lower alkyl, lower alkoxy, lower thioalkyl, trifluoromethyl, lower acyloxy, aryl, heteroaryl, and hydroxy. Preferred aryl groups include phenyl and naphthyl, each of which is optionally substituted as defined herein.

By "aryloxy" is meant —O-aryl.

By "substituted aryloxy" is meant —O-substituted aryl.

By "aralkyl" is meant the groups -alkylene-aryl, -alkylene substituted aryl, -substituted alkylene-aryl and -substituted alkylene-substituted aryl.

By "carboxyl" or "carboxy" is meant —COOH and salts thereof.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, and benzoxazolyl. Preferred heteroaryls are thiazolyl, pyrimidinyl, preferably pyrimidin-2-yl, and pyridyl. Other preferred heteroaryl groups include 1-imidazolyl, 2-thienyl, 1-(or 2-)quinolinyl, 1-(or 2-) isoquinolinyl, 1-(or 2-)tetrahydroisoquinolinyl, 2-(or 3-)furanyl and 2-tetrahydrofuranyl.

By "substituted heteroaryl" is meant a heteroaryl group having from 1 to 3 and preferably one substituted as defined above for substituted aryl.

By "heteroaralkyl" is meant the groups -alkylene-heteroaryl, -alkylene substituted heteroaryl, -substituted alkylene-heteroaryl and -substituted alkylene-substituted heteroaryl.

By "heterocyclic" or "heterocycle" or "heterocyclyl" is meant refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is to a heterocyclic ring atom.

By "substituted heterocyclic" is meant a heterocycle group that is substituted with from 1 to 3 and preferably 1 substituent of the same substituents as defined for substituted cycloalkyl.

By "thiol" is meant —SH.

By "thioalkyl" is meant —S-alkyl. By "thio-lower alkyl" is meant —S-lower alkyl.

By "substituted alkylthio" is meant —S-substituted alkyl.

By "arylthio" is meant —S-aryl.

By "substituted arylthio" is meant —S-substituted aryl.

The term "aromatic ring" refers to optionally substituted aryl groups and optionally substituted heteroaryl groups.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl. Impermissible substitution patterns are not permissible.

By "ligand" is meant a nitrogen-containing aromatic system that is capable of forming a dative bond with the Lewis acidic boron center, while appended as a borinate ester moiety. Such ligands are known to those trained in the arts. Examples are shown in the structures below

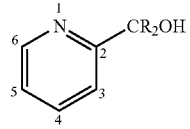

2- hydroxymethylpyridine R = H
2-(hydroxyisopropyl)pyridine R = Me

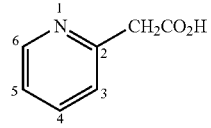

2-pyridylacetic acid

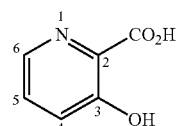

3-hydroxypicolinic acid

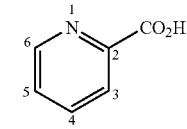

picolinic acid
(pyridine-2-carboxylic acid)

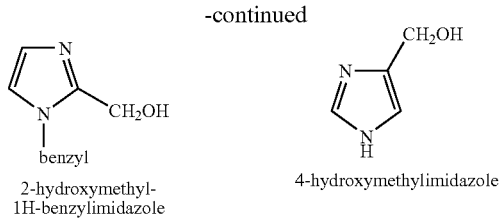

2-hydroxymethyl-1H-benzylimidazole 4-hydroxymethylimidazole

The compounds of the present invention have been implicated in the inhibition of key microbial enzymes, such as bacterial methyltransferases. Many of the compounds disclosed herein are selective inhibitors of methyltransferases in microbes, while not inhibitory for methyltransferases in mammals. However, the antibacterial of the compounds of the invention is not limited to those with said enzyme inhibitory activity, nor is the latter effect necessarily essential to said therapeutic activity.

The invention also provides embodiments of the compounds disclosed herein as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, hydroxyethanesulfonic, nitric, benzoic, citric, tartaric, maleic, hydroiodic, alkanoic such as acetic, HOOC—$(CH_2)_r$—$CH_3$ where r is 0-4, and the like. Non-toxic pharmaceutical base addition salts include salts of bases such as sodium, potassium, calcium, ammonium, and functional equivalents. Those skilled in the art will recognize a wide variety of non-toxic pharmaceutically acceptable addition salts. For injection, the compounds of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For topical administration, the compounds can be formulated readily by combining the active compounds with pharmaceutically acceptable carriers well known in the art. Such carriers enable the compounds of the invention to be formulated as gels, slurries, suspensions and ointments for topical applications. If desired, disintegrating agents can be added, such as the cross-linked polyvinyl pyrrolidone, agar, or alginic acid or a salt thereof such as sodium alginate.

A pharmaceutical carrier for the hydrophobic compounds of the invention is a co-solvent system comprising benzyl alcohol, a nonpolar surfactant, a water-miscible organic polymer, and an aqueous phase. The co-solvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g., polyvinyl pyrrolidone, and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethyl sulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. The compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitric, benzoic, citric, tartaric, maleic, hydroiodic, alkanoic such as acetic, HOOC—$(CH_2)$r-$CH_3$ where r is 0-4, and the like. Salts tend to be more soluble in aqueous or other protic solvents than are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the compounds of the present invention can be formulated and administered through a variety of means, including systemic, localized, or topical administration. Techniques for formulation and administration can be found in *Remington's Pharmaceutical Sciences*, Mack Publishing Co., Easton, Pa. The mode of administration can be selected to maximize delivery to a desired target site in the body. Suitable routes of administration can, for example, include oral, rectal, transmucosal, transcutaneous, or intestinal administration. Parenteral delivery, including intramuscular, subcutaneous, and intramedullary injections, as well as intrathecal, direct intraventricular, intravenous, intraperitoneal, intranasal, or intraocular injections are also contemplated.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the methods of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

It is contemplated that the preferred compounds of the invention may have certain pharmacological properties. Such properties include, but are not limited to, oral bioavailability, low toxicity, low serum protein binding and desirable in vitro and in vivo half-lives. Assays may be used to predict these desirable pharmacological properties.

Assays used to predict bioavailability include transport across human intestinal cell monolayers, including Caco-2 cell monolayers. Serum protein binding may be predicted from albumin binding assays. Such assays are described in a review by Oravcová, et al. (1996, *J. Chromat.* B 677:1-27). Compound half-life is inversely proportional to the frequency of dosage of a compound. In vitro half-lives of compounds may be predicted from assays of microsomal half-life as described by Kuhnz and Gieschen (*Drug Metabolism and Disposition*, (1998) volume 26, pages 1120-1127).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in *The Pharmacological Basis of Therapeutics*, Ch. 1, p. 1). Dosage amounts and intervals can be adjusted individually to provide plasma levels of the active moiety that are sufficient to maintain bacterial cell growth inhibitory effects. Usual patient dosages for systemic administration range from 100-2000 mg/day. Stated in terms of patient body surface areas, usual dosages range from 50-910 mg/m$^2$/day. Usual average plasma levels should be maintained within 0.1-1000 µM. In cases of local administration or selective uptake, the effective local concentration of the compound cannot be related to plasma concentration.

In accordance with the foregoing, the present invention relates to a method of treating and/or preventing a surface infection in an animal, preferably a human patient, comprising administering to an animal, or patient, afflicted with such surface infection, or at risk of becoming so afflicted, an effective amount (i.e., a therapeutically effective amount) of a compound having the structure of Formula 1 or Formula 2. In preferred embodiments of such method, the compound is an antibiotic as disclosed herein, preferably one having any of the preferred substituents, or combinations of substituents, as recited according to the present invention.

In one preferred embodiment, the surface infection is an inflammation of skin. In other embodiments, such surface infection, or surface condition, may afflict some other part of the body, such as the lungs or alimentary canal, especially the oral or anal cavities thereof, wherein the surface of such organ is a site of infection.

In a preferred embodiment, the inflammation is one of acne vulgaris, acne rosacea, psoriasis, atopic dermatitis, periodontal disease, asthma, chronic obstructive pulmonary diseases (COPD), an inflammatory bowel disease, or arthritis, more preferably acne, and most preferably acne vulgaris or acne rosacea.

In another preferred embodiment, the inflammation is psoriasis. In a further preferred embodiment, the inflammation is asthma.

In an additional preferred embodiment, the inflammation is arthritis. The present invention also relates to methods of blocking the production of pro-inflammatory cytokines in an animal, preferably a human patient, an effective amount of a compound disclosed hereinabove for use in any of the other methods of the invention and having the same preferred structures. In a preferred embodiment of the foregoing, the cytokine is one or more of IL-1β (interleukin 1β), TNF (tumor necrosis factor)-α, IL-6 and IL-8.

The disclosures in this application of all articles and references, including patents and patent applications, are incorporated herein by reference in their entirety. In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer systems or culture media for another and still achieve similar, if not identical, results. Those skilled in the art will have sufficient knowledge of such systems and methodologies so as to be able, without undue experimentation, to make such substitutions as will optimally serve their purposes in using the methods and procedures disclosed herein.

5 EXAMPLES

The invention is described in more detail in the following non-limiting examples. It is to be understood that these methods and examples in no way limit the invention to the embodiments described herein and that other embodiments and uses will no doubt suggest themselves to those skilled in the art.

The compounds of this invention are evaluated for their antibacterial activity as per the guidelines and procedures prescribed by the National Committee for Clinical Laboratory Standards (NCCLS) (cf., NCCLS Document M7-A3, 1993-*Antimicrobial Susceptibility Testing*).

5.1 MIC Determination 5.1.1 Protocol for Determining Minimum Inhibitory Concentration (MIC)

A useful protocol for MIC determination is as follows:
1. Approximately 2.5 mg of the compounds to be tested was weighed into cryovials.
2. 5 mg/ml stock solutions were made by adding DMSO to the samples accordingly.
3. 256 μg/ml working solutions were made by using the 5 mg/ml stock solutions and adding sterile distilled water accordingly.
4. A Beckman 2000 Automated Workstation was programmed to load 96-well plates with broth and compounds as follows:
   100 μl of the appropriate broth was added to columns 1-11.
   200 μl of the appropriate broth was added to column 12.
   100 μl of compounds at the 256 μg/ml working solution were added to column 1 (one compound per row).
   Two-fold serial dilutions were done from columns 1-10.
   Column 11 served as the growth control.
5. The ten-organism panel was plated from stock vials stored at −80° C. and incubated for 24 hours at 34° C. The organisms were then sub-cultured and incubated for 24 hours at 34° C.
   The inoculums were first prepared in sterile distilled water with a target of 0.09-0.11 absorbance at 620 nm wavelength.
   A 1/100 dilution was made into the appropriate broth.
   100 μl of broth with organism was added to columns 1-11.
   Column 12 served as the blank control.
6. The completed 96 well plates were incubated for 24 hours at 34° C. The 96-well plates were then read using a Beckman Automated Plate Reader at 650 nm wavelength. The MIC was determined through calculations involving the growth control (column 11) and blank control (column 12).

5.1.2 MIC Calculation

The absorbance readings from the Biomek Automated Plate Reader are used to determine the percent inhibition for each test well. The formula used is as follows:

$$\% \text{ Inhibition} = \left[ \frac{1 - (ABS_{Test} - ABS_{Blank})}{(ABS_{Growth} - ABS_{Blank})} \right] \times 100$$

$ABS_{Test}$: Absorbance of the test well.
$ABS_{blank}$: Absorbance of the blank well in the same row as the test well (column 12).
$ABS_{growth}$: Mean absorbance of the growth control wells (column 11).

The minimum inhibitory concentration (MIC) is found at the lowest concentration of compound where percent inhibition is greater than or equal to 80%.

These procedures were used to obtain the representative microbiological data for the compounds 10 to 19 shown in Table 1 as MIC (Minimum Inhibitory Concentration) with the values expressed as micrograms per milliliter (mcg/ml).

5.2 Inhibition of IL-β, IL-6, or TNF-α Secretion from Human Peripheral Blood Monocytes (PBMC) Stimulated with LPS PBMC ($5 \times 10^5$ cells) suspended in RPMI 1640 culture medium supplemented with 1% penicillin and 1% streptomycin are pre-incubated for 30 min. at 37° C. with the test compound, reference compound, or culture medium (control). Thereafter, 1 μg/ml LPS is added to induce the cytokine secretion and the mixture is incubated for 24 h at 37° C. For basal control measurements, LPS is omitted from the incubation medium. Following incubation, the samples are centrifuged at 250×g for 5 min. at 4° C. and the supernatants are collected. The amount of secreted IL-1β, 1L-6, or TNF-α present in the supernatant is quantified using an EIA detection kit (R&D systems). The photometric measurements are made with a microplate reader (Ultra, Tecan). The results are expressed as a percent inhibition of the control secretion induced by LPS. The standard inhibitory reference compounds for IL-1β, IL-6 or TNF-α are cycloheximide and dexamethasone, respectively, which are tested in each experiment at several concentrations to obtain an inhibition curve from which their $IC_{50}$ values are calculated (Schindler, R., et al., (1990). "Correlations and interactions in the production of interleukin-6 (IL-6), IL-1, and tumor necrosis factor (TNF) in human blood mononuclear cells: IL-6 suppresses IL-1 and TNF", *Blood*, 75:40.

These procedures were used to determine the inhibition (and selectivity) of cytokine release by representative compounds 10 to 11 shown in Table 2. Thus, the invention provides antibiotics that are generically called borinic acid complexes, most preferably derived from disubstituted borinic acids.

5.3 Borinate Complexes 5.3.1 Synthetic Overview

The synthesis of the compounds of the invention is accomplished in several formats. Reaction Scheme 1 demonstrates the synthesis of the intermediate borinic acids, and their subsequent conversion to the desired borinic acid complexes. When R* and R** are identical, the reaction of two equivalents of an aryl magnesium halide (or aryl lithium) with trialkyl borate, followed by acidic hydrolysis affords the desired borinic acid 5. When R* and R** are not identical, the reaction of one equivalent of an aryl magnesium halide (or aryl lithium) with appropriate aryl(dialkoxy)borane (4), heteroaryl(dialkoxy)borane or alkyl (dialkoxy)borane (alkoxy group comprised of methoxy, ethoxy, isopropoxy, or propoxy moiety), followed by acidic hydrolysis affords the unsymmetrical borinic acids 6 in excellent yields. Where applicable, the reaction of the alkylene esters (3, T=single bond, $CH_2$, $CMe_2$) with the appropriate organocerium, organolithium, organomagnesium or equivalent reactant is convenient.

As shown in Scheme 1, the boronic acid complexes are obtained from the precursor borinic acids by reaction with one equivalent of the desired heterocyclic ligand in suitable solvents (i.e., ethanol, isopropanol, dioxane, ether, toluene, dimethylformamide, N-methylpyrrolidone, or tetrahydrofuran).

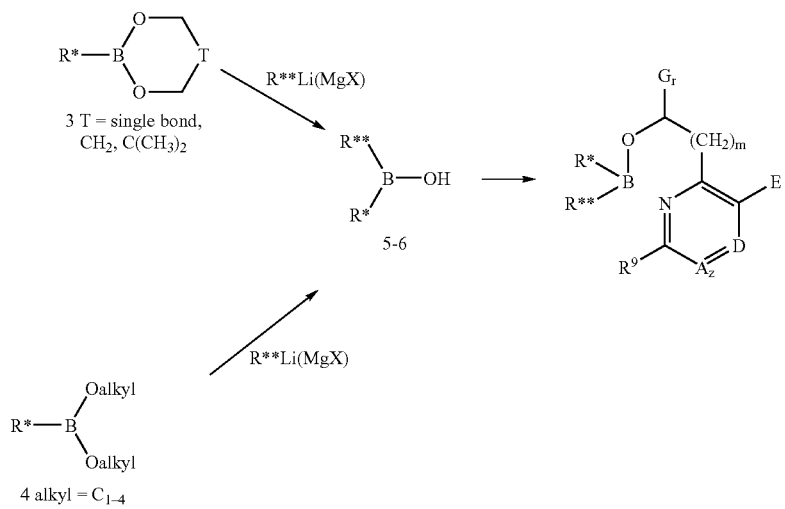

Scheme 1

In certain situations, compounds of the invention may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column. Representative compounds of the present invention include, but are not limited to the compounds disclosed herein and their pharmaceutically acceptable acid and base addition salts. In addition, if the compound of the invention is obtained as an acid addition salt, the free base can be obtained by basifying solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid 5 addition salts from base compounds. In a preferred embodiment, the compounds of the invention comprise any of compounds 10-16 (described below), and variants thereof. Table 1 also contains inhibitory activity for a antibiotic.

TABLE 1

Anti-gram-positive In vitro Activity

MIC (mcg/mL)

| Compound | P. acnes ATCC 6919 | S. epidermidis ATCC 12228 | S. aureus ATCC 29213 |
|---|---|---|---|
| 10 | 0.3 | 1 | 2 |
| 11 | 0.3 | 0.25 | 1 |
| 12 | 3 | 1 | 0.5 |
| 13 | 3 | 1 | 2 |
| 14 | 3 | 4 | 0.125 |
| 15 | 3 | 4 | 4 |
| 16 | 10 | 8 | 0.5 |
| erythromycin | 1–2 | r 0.5 | 0.5 |

The present invention also encompasses the acylated prodrugs of the compounds of the invention. Those skilled in the art will recognize various synthetic methodologies that may be employed to prepare non-toxic pharmaceutically acceptable addition salts and acylated prodrugs of the inventive compounds.

The selective inhibition of the release of pro-inflammatory cytokines is shown in Table 2 with representative compounds 10, 11, and 30-35. In general, useful compounds of the invention demonstrate at least 10% inhibition of the pro-inflammatory cytokine in question at a concentration of 25 µM or have a corresponding $IC_{50}$ value thereto.

TABLE 2

Selective Pro-inflammatory Cytokine Release

| | $IC_{50}$ (µM) or Inhibition (%) at 25 µM Pro-inflammatory Cytokines | | | |
|---|---|---|---|---|
| Compound | TNF-α | IL-1β | IL-6 | IL-8 |
| 10 | 8.6 (100%) | 10.8 (99%) | 3.6 (80%) | (122%) |
| 11 | 14.9 (101%) | 15 (103%) | 2.8 (102%) | (122%) |
| 30 | 101% | 76% | | |
| 31 | 101% | 80% | | |
| 32 | 101% | 34% | | |
| 33 | 48% | 60% | | |
| 34 | 101% | 100% | 108% | |

5.3.2 SPECIFIC SYNTHETIC EXAMPLES

5.3.2.1 Common Synthetic Procedures

Proton NMR were recorded on Varian AS 400 spectrometer and chemical shifts are reported as δ (ppm) down field from tetramethylsilane. Mass spectra are determined on Micromass Quattro U. Compound numbers appear in parentheses and correspond to numbers in Tables 1 and 2.

5.3.2.1.1 Formation of Ethylene Glycol Boronate Esters (3, T=Single Bond) General Procedure Boronic acid was dissolved in dry THF or dry diethyl ether (~10 mL/g) under nitrogen. Ethylene glycol 1 molar equivalent) was added to the reaction and the reaction was heated to reflux for 1 to 4 hours. Reaction was cooled to room temperature and solvent was removed under reduced pressure leaving the ethylene glycol ester as an oil or a solid. In cases where an oil was obtained or a solid that dissolved in hexane, dry hexane was added and removed under reduced pressure. The product was then placed under high vacuum for several hours. In cases where a solid was obtained that did not dissolve in hexane, the solid was collected by filtration and washed with cold hexane.

5.3.2.1.1.1 Cyanophenylboronic Acid Ethylene Glycol Ester (3a)

3-Cyanophenyl boronic acid (1 g, 6.8 mmol) was dissolved in dry THF (10 mL) under nitrogen. Ethylene glycol (379 µL, 422 mg, 6.8 mmol) was added and the reaction was heated to reflux for 4 hours then cooled to room temperature. THF was removed by rotary evaporator to give a white solid. Cold hexane was added and the product was collected by filtration giving a white solid (1.18 g, quant. yield). $^1$H-NMR (300.058 MHz, DMSO-d6) δ ppm 7.92-8.01 (3H, m), 7.50-7.64 (1H, m), 4.35 (4H, s)

5.3.2.1.1.2 Thiophene 3-Boronic Acid Ethylene Glycol Ester (3b)

Thiophene-3-boronic acid (1 g, 7.8 mmol) was dissolved in dry THF (10 mL) under nitrogen. Ethylene glycol (435 µL, 484 mg, 7.8 mmol) was added and the reaction was heated to reflux for 1 hour then cooled to room temperature. THF was removed by rotary evaporator to give a white solid. Hexane was added, dissolving the solid and removed by rotary evaporation. The product was placed under high vacuum to yield a tan solid (1.17 g, 97%). $^1$H-NMR (300.058 MHz, CDCl$_3$) δ ppm 7.93 (1H, s), 7.3-7.4 (2H, m), 4.35 (4H, s).

5.3.2.2 Formation of Unsymmetrical Borinic Acid (6) from Boronic Acid Ethylene Glycol Ester General Procedure A: Grignard Methodology Boronic acid ethylene glycol ester was dissolved in dry THF (10-20 mL/g) under nitrogen. Solution was cooled to −78° C. in an acetone-dry ice bath or to 0° C. in an ice/water bath. Grignard reagent (0.95- to 1.2 molar equivalent) was added drop-wise to the cooled solution. The reaction was warmed to room temperature and stirred for 3-18 hours. 6 N HCl (2 mL/g) was added and solvent was removed under reduced vacuum. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification. Alternative work-up: if the borinic acid product contained a basic group such as an amine or pyridine, then after stirring at room temperature for 3-18 hours, water (2 mL/g) was added and the pH adjusted to 5-7. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification.

5.3.2.2.1 (4-cyanophenyl)(3-fluorophenyl)borinic acid (6a)

4-Cyanophenyl boronic acid ethylene glycol ester (500 mg, 2.89 mmol) was dissolved in dry THF under nitrogen. The solution was cooled to −78° C. in an acetone/dry ice bath and 3-fluorophenylmagnesium bromide (1 M in THF, 2.74 mL, 2.74 mmol, 0.95 molar equivalent) was added drop-wise to the cold solution. The reaction was allowed to warm slowly to room temperature and stirred for 18 hours. 6 N HCl (1 mL) was added to the reaction causing a cloudy appearance and the solvent was removed using a rotary evaporator. The product was extracted into diethyl ether (20 mL) and washed with water (3×20 mL). The organic layer was dried (MgSO$_4$), filtered and the solvent removed using a rotary evaporator to yield the crude product as an oily solid. This was taken onto the next step without purification.

5.3.2.3 General Procedure B: (Hetero)Aryl-Lithium Methodology

The (hetero)aryl-bromide or iodide was dissolved in dry THF (20-30 mL/g) under nitrogen and degassed. The solution was cooled to −78° C. in an acetone/dry ice bath and n-, sec- or tert-butyllithium in THF or other solvent (1.5-2.4 molar equivalents) was added to the cooled solution drop-wise generally causing the solution to turn deep yellow. The boronic acid ethylene glycol ester (1 molar equivalent) was dissolved in dry THF or diethyl ether (2-5 mL/g) under nitrogen. The boronic acid ethylene glycol ester in THF was added drop-wise to the cooled aryl-lithium solution generally causing the solution to turn pale yellow. The reaction was warmed to room temperature and stirred for 3-18 hours. 6N HCl (2-4 mL/g) was added and solvent was removed under reduced vacuum. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification. Alternative work-up: if the borinic acid product contained a basic group such as an amine or pyridine then after stirring at room temperature for 3-18 hours water (2 mL/g) was added and the pH adjusted to 5-7. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification.

5.3.2.3.1 (3-thienyl)(3-chlorophenyl)borinic acid (6b)

3-Chloro-bromobenzene (447 µL, 728 mg, 3.8 mmol) was dissolved in dry THF (15 mL) under nitrogen. The solution was degassed and cooled to −78° C. in an acetone/dry ice bath, tent-Butyllithium (1.7 M in THF) (4.47 mL, 7.6 mmol, 2 molar equivalent) was added to the cooled solution drop-wise causing the solution to turn deep yellow. The solution was stirred at −78° C. while 3-thiopheneboronic acid ethylene glycol ester (586 mg) was dissolved in dry diethyl ether (1 mL). The boronic ester solution was then added drop-wise to the coaled solution causing the color to change to pale yellow.

The reaction was warmed to room temperature and stirred for 18 hours. 6 N HCl (2 mL) was added and the reaction was stirred for 1 hour. The solvent was removed using a rotary evaporator. The product was extracted into diethyl ether (10 mL) and washed with water (2×10 mL). The organic layer was dried (MgSO$_4$), filtered and the solvent removed using a rotary evaporator to yield the crude product as an orange oil. The product was purified by column chromatography using silica gel and hexane:ethyl acetate 5:1 as eluent giving the pure product as a clear oil (614 mg, 73%).

5.3.2.3.2 (3-chlorophenyl)vinyl borinic acid (6c)

This was prepared by a similar process as described for 6b by the reaction of 3-cyanophenyl boronic acid ethylene glycol ester with vinyl lithium.

5.3.2.3.3 (3-fluoro-5-chlorophenyl)ethynyl borinic acid (6d)

This was prepared by a similar process as described for 6b by the reaction of 3-fluoro-5-chlorophenyl boronic acid ethylene glycol ester with ethynyl lithium.

5.3.2.3.4 (4-methyl-3-chlorophenyl)(2-thienyl)borinic acid (6e)

This was prepared by a similar process as described for 6b by the reaction of 2-thienylboronic acid ethylene glycol ester with 4-methyl-3-chlorophenyllithium.

5.3.2.3.5 (4-cyanophenyl)ethynyl borinic acid (6f)

This was prepared by a similar process as described for 6b by the reaction of 4-cyanophenylboronic acid ethylene glycol ester with ethynyl lithium.

5.3.2.3.6 (3-fluorophenyl)cyclopropylborinic acid (6g)

This was prepared by a similar process as described for 6b by the reaction of 3-fluorophenylboronic acid ethylene glycol ester with cyclopropyl lithium.

5.3.2.3.7 (3-thienyl)methyl borinic acid (6h)

This was prepared by a similar process as described for 6b by the reaction of 3-thienylboronic acid ethylene glycol ester with methyl lithium.

5.3.2.3.8 (4-pyridyl)phenyl borinic acid (6i)

This was prepared by a similar process as described for 6b by the reaction of phenylboronic acid ethylene glycol ester with 4-pyridyllithium.

5.3.2.3.9 (3-cyanophenyl)(2-fluorophenyl)borinic acid (6j)

This was prepared by a similar process as described for 6b by the reaction of 3-cyanophenylboronic acid ethylene glycol ester with 2-fluorophenyllithium.

5.3.2.4 Formation of Symmetrical Borinic Acid (5) by Reaction of Organometallics with Trialkyl Borates

5.3.2.4.1 bis(4-chlorophenyl)borinic acid (5a) (Procedure C)

A cold solution (−78° C.) of trimethyl borate (0.37 mL) in dry tetrahydrofuran (THF, 25 mL) was treated drop-wise with 4-chlorophenylmagnesium bromide (6.75 mL, 1 M solution in ether). The reaction mixture was stirred at −78° C. for 1 h and then stirred for 18 h at room temperature. The solvent was removed under reduced pressure. The resultant residue was stirred with 100 mL of ether and 15 mL of 6 N hydrochloric acid. Organic layer was separated and aqueous layer was extracted with ether (2×100 mL). The combined organic extract was washed with brine and dried over anhydrous magnesium sulfate. Solvent was removed to give light yellowish solid. The product was chromatographed over silica gel (Hex:Ether=1:1) to give 420 mg of borinic acid. $^1$H-NMR (400 MHz, CDCl$_3$) δ: 5.84 (s, OH), 7.46 (d, 4H, Ar—H), 7.72 (d, 4H, Ar—H).

5.3.2.4.2 Bis(3-chloro-4-methylphenyl)borinic acid (5b)

In a similar manner as for 5a, the titled compound was obtained from the reaction of 3-chloro-4-methylphenylmagnesium bromide with trimethyl borate. The product was obtained by chromatography over silica gel.

5.3.2.4.3 Bis(3-fluoro-4-methylphenyl)borinic acid (5c)

In a similar manner as for 5a, the titled compound was obtained from the reaction of 3-fluoro-4-methylphenyllithium with trimethyl borate. The product was obtained by chromatography over silica gel.

5.3.2.4.4 Bis(3-chloro-4-methoxyphenyl)borinic acid (5d)

In a similar manner as for 5a, the titled compound was obtained from the reaction of 3-chloro-4-methoxyphenyllithium with trimethyl borate. The product was obtained by chromatography over silica gel.

5.3.2.4.5 Bis(3-fluoro-4-methoxyphenyl)borinic acid (5e)

In a similar manner as for 5a, the titled compound was obtained from the reaction of 3-fluoro-4-methoxyphenyllithium with trimethyl borate. The product was obtained by chromatography over silica gel.

5.3.2.5 Formation of Unsymmetrical Borinic Acids (6) by Reaction of Organometallics with Alkyl(Aryl)Dialkoxyboranes

5.3.2.5.1 (4-chlorophenyl)methylborinic acid (6k) (Procedure D)

To 4-chlorophenylmagnesium bromide (5.5 mL, 1 M solution in ether) at −78° C., di(isopropoxy)methylborane (1 mL, 0.78 g) was added drop-wise by syringe. The reaction mixture was stirred at −78° C. for 1 h and then stirred overnight at ambient temperature. The reaction mixture was treated drop-wise with 100 mL of ether and 15 mL of 6 N hydrochloric acid, and stirred for 1 h. Organic layer was separated and aqueous layer was extracted with ether (2×100 mL). The combined organic extract was washed with brine and dried over anhydrous sodium sulfate. Solvent was removed under reduce pressure to give 1.1 g of oil. $^1$H-NMR of the product was consistent for (4-chlorophenyl)methyl borinic acid.

5.3.2.5.2 (4-fluorophenyl)methylborinic acid (6m)

In a similar manner as for 6k, the titled compound was obtained from the reaction of 4-fluorophenylmagnesium bromide with di(isopropoxy)methylborane. The product was obtained by chromatography over silica gel.

5.3.2.5.3 (4-biphenyl)methylborinic acid (6n)

In a similar manner as for 6k, the titled compound was obtained from the reaction of 4-biphenyllithium with di(isopropoxy)methylborane. The product was obtained by chromatography over silica gel.

5.3.2.5.4 (3-chloro-4-methylphenyl)methylborinic acid (6o)

In a similar manner as for 6k, the titled compound was obtained from the reaction of 3-chloro-4-methylphenyllithium with di(isopropoxy)methylborane. The product was obtained by chromatography over silica gel.

5.3.2.5.5 (3-chloro-4-methoxyphenyl)methylborinic acid (6p)

In a similar manner as for 6k, the titled compound was obtained from the reaction of 3-chloro-4-methoxyphenyllithium with di(isopropoxy)methylborane. The product was obtained by chromatography over silica gel.

5.3.2.5.6 (4-dimethylaminophenyl)methylborinic acid (6q)

In a similar manner as for 6k, the titled compound was obtained from the reaction of 4-dimethylaminophenyllithium with di(isopropoxy)methylborane. The product was obtained by chromatography over silica gel.

5.3.2.5.7 (3-chloro-4-dimethylaminophenyl)vinylborinic acid (6r)

In a similar manner as for 6k, the titled compound was obtained from the reaction of 3-chloro-4-dimethylaminophenyllithium with di(butoxy)vinylborane. The product was obtained by chromatography over silica gel.

5.3.3 PICOLINATE DERIVATIVES

5.3.3.1 Bis(3-chloro-4-methylphenyl)borinic acid 3-hydroxypicolinate ester (10)

Bis(3-chloro-4-methylphenyl)borinic acid (14.6 g) was dissolved in ethanol (120 mL) and heated to reflux. 3-Hydroxypicolinic acid (5.83 g) was added in portions to the hot solution. The reaction was stirred at reflux for 15 minutes after the last portion of 3-hydroxypicolinic acid was added and then cooled to room temperature. The reaction was concentrated by removal of some of the volatiles. The solid was removed by filtration. One recrystallization from ethanol afforded the title product as white crystals (13.4 g) mp=165.0-166.5° C. MS (ESI+): m/z=400 (M$^+$+1).

5.3.3.2 Bis(2-methyl-4-chlorophenyl)borinic acid 3-Hydroxypicolinate ester (11)

In a similar manner as in Section 5.3.3.1, the titled compound was prepared from bis(2-methyl-4-chlorophenyl)borinic acid and 3-hydroxypicolinic acid to afford a white crystalline solid. MS (ESI+): m/z=400 (M$^+$+1).

5.3.3.3 (3-chloro-4-methylphenyl)(phenethyl)borinic acid 3-Hydroxypicolinate ester (12)

In a similar manner as in Section 5.3.3.1, the titled compound was prepared from (3-chloro-4-methylphenyl)(phenethyl)borinic acid and 3-hydroxypicolinic acid to afford a white crystalline solid. MS (ESI+): m/z=378 (M$^+$+1).

5.3.3.4 (3-Bromo-6-chloro-2-fluorophenyl)(2-fluoro-4-chlorophenyl)borinic acid 3-Hydroxypicolinate ester (13)

In a similar manner as in Section 5.3.3.1, the titled compound was prepared from (2-bromo-6-chloro-2-fluorophenyl)(2-fluoro-4-chlorophenyl)borinic acid and 3-hydroxypicolinic acid to afford a white crystalline solid. MS (ESI+): m/z=488 (M$^+$+1).

5.3.3.5 Bis(2-Chloro-4-methylphenyl)borinic acid 3-carboxypicolinate ester (14)

In a similar manner as in Section 5.3.3.1, the titled compound was prepared from bis(2-chloro-4-methylphenyl)borinic acid and pyridine-2,3-dicarboxylic acid to afford a white crystalline solid. MS (ESI+): m/z=426 (M$^+$+1).

5.3.3.6 (2-Methoxy-5-chlorophenyl)(3-chlorophenyl)borinic acid 3-Hydroxypicolinate ester (15)

In a similar manner as in Section 5.3.3.1, the titled compound was prepared from (2-methoxy-5-chlorophenyl)(3-chlorophenyl)borinic acid and 3-hydroxypicolinic acid to afford a white crystalline solid. HPLC: 95.6% purity at 220 nm.

5.3.3.7 Bis(3-chlorophenyl)borinic acid 6-Acetylamino-3-hydroxypicolinate ester (16)

In a similar manner as in Section 5.3.3.1, the titled compound was prepared from bis(3-chlorophenyl)borinic acid and 6-acetylamino-3-hydroxypicolinic acid to afford a white crystalline solid. MS (ESI+): m/z=429 (M$^+$+1).

5.3.3.8 Bis(3-chloro-4-methylphenyl)borinic Acid 3-(Ethyloxycarbonyl)picolinate Ester (30)

In a similar manner as in Section 5.3.3.1, the titled compound was prepared from bis(3-chloro-4-methylphenyl)borinic acid and 3-carboxypicolinic acid to afford a white crystalline solid. ESI-MS m/e 456 (M+H)$^+$, $C_{23}H_{20}B^{35}Cl_2NO_4$=455.

5.3.3.9 Bis(3-chloro-4-methylphenyl)borinic acid 5-Carboxypicolinate ester (31)

In a similar manner as in Section 5.3.3.1, the titled compound was prepared from bis(3-chloro-4-methylphenyl) borinic acid and 5-carboxypicolinic acid to afford a white crystalline solid. ESI-MS m/e 426 (M–H)$^-$, $C_{21}H_{16}B^{35}Cl_2NO_4$=427.

5.3.3.10 Bis(3-chloro-4-methylphenyl)borinic acid 3-[(2-Morpholinoethyl)oxy]picolinate ester (32)

In a similar manner as in Section 5.3.3.1, the titled compound was prepared from bis(3-chloro-4-methylphenyl) borinic acid and 3-(2-hydroxyethoxy)picolinic acid to afford a white crystalline solid. ESI-MS m/e 513 (M+H)$^+$, $C_{26}H_{27}B^{35}Cl_2N_2O_4$=512.

5.3.3.11 (3-chloro-4-methylphenyl)(4-hydroxyphenyl)borinic acid 3-hydroxypicolinate ester (33)

In a similar manner as in Section 5.3.3.1, the titled compound was prepared from (3-chloro-4-methylphenyl)(4-hydroxyphenyl) borinic acid and 3-hydroxypicolinic acid to afford a white crystalline solid. ESI-MS m/e 366 (M–H)$^-$, $C_{19}H_{15}B^{35}ClNO_4$=367.

5.3.3.12 (3-Bromo-6-chloro-2-fluorophenyl)(4-chloro-2-fluorophenyl)borinic acid 3-hydroxypicolinate ester (34)

In a similar manner as in Section 5.3.3.1, the titled compound was prepared from (3-Bromo-6-chloro-2-fluorophenyl)(4-chloro-2-fluorophenyl)borinic acid and 3-hydroxypicolinic acid to afford a white crystalline solid. ESI-MS m/e 487, 485 (M–H)$^-$, $C_{18}H_9B^{79}Br^{35}Cl_2FNO_3$=486.

5.3.3.13 (4-Chlorophenyl)(4-dimethylaminophenyl) borinic acid 3-Hydroxypicolinate ester (35)

In a similar manner as in Section 5.3.3.1, the titled compound was prepared from (4-chlorophenyl)(4-dimethylaminophenyl) borinic acid and 3-hydroxypicolinic acid to afford a white crystalline solid. ESI-MS m/e 393 (M–H)$^-$, $C_{21}H_{20}B^{35}ClN_2O_3$=394.

5.3.3.14 (3-Chlorophenyl)[4-(morpholin-4-ylmethyl)phenyl]borinic acid 3-Hydroxypicolinate ester (36)

In a similar manner as in Section 5.3.3.1, the titled compound was prepared from (3-chlorophenyl)[4-(morpholin-4-ylmethyl)phenyl]borinic acid and 3-hydroxypicolinic acid to afford a white crystalline solid. ESI-MS m/e 435 (M–H)$^-$, $C_{23}H_{22}B^{35}ClN_2O_4$=436.

5.3.3.15 (4-Chlorophenyl)[4-[2-(dimethylamino)ethoxy]phenyl]borinic acid 3-Hydroxypicolinate ester (37)

In a similar manner as in Section 5.3.3.1, the titled compound was prepared from (4-chlorophenyl)[4-[2-(dimethylamino)ethoxy]phenyl]borinic acid and 3-hydroxypicolinic acid to afford a white crystalline solid. ESI-MS m/e 423 (M–H)$^-$, $C_{22}H_{22}B^{35}ClN_2O_4$=424.

5.3.3.16 (4-Chlorophenyl)(2-chloroprydin-5-yl) borinic acid 3-Hydroxypicolinate ester (38)

To a solution of 5-bromo-2-chloropyridine (2.75 g) and 4-chlorophenylboronic acid ethylene glycol ester (2.60 g) in dry THF (150 mL) was added n-butyllithium (1.6 M in hexanes, 10 mL) over 1 h, and the mixture was stirred at –78° C. for 2 h and room temperature for overnight. Ether (150 mL) was added, and the pH was adjusted at 2 with 6 N HCl at –20° C. The mixture was allowed to warm to room temperature and stirred for 2 h. The pH was adjusted to 8, and the two layers were separated. The aqueous layer was extracted with ether. The organic layers were combined. To the organic layer was added a solution of 3-hydroxypicolinic acid (1.00 g) in ethanol (20 mL) and water (10 mL), and the mixture was stirred at room temperature for overnight. The precipitated formed were filtered off, washed with water and ether to give the product as white solid (580 mg): ESI-MS m/z 373 (M+H)$^+$, $C_{17}H_{11}B^{35}Cl_2N_2O_3$=372.

5.3.4 Imidazole Derivatives

5.3.4.1 Bis(3-chlorophenyl)borinic acid 4-(hydroxyethyl)imidazole ester (20)

To a solution of bis(3-chlorophenyl)borinic acid (0.4 g, 1.428 mmol) in ethanol (10 mL), 4-(hydroxyethyl)imidazole hydrochloride (0.191 g, 1.428 mmol), sodium bicarbonate (0.180 g, 2.143 mmol) were added and the reaction mixture was stirred at room temperature for 18 h. Salt was removed by filtration. Filtrate was concentrated and treated with hexane to afford the product as a solid and was collected by filtration. (450 mg, 84.9% yield). MS (ESI–): m/z=343 (M$^-$–1).

5.3.4.2 Bis(4-Chlorophenyl)borinic acid 4-(hydroxymethyl)imidazole ester (21)

In a similar manner as in Section 5.3.3.1, the titled compound was obtained from the reaction of bis(4-chlorophenyl) borinic acid with 4-(hydroxymethyl)imidazole hydrochloride as white crystals. MS (ESI–): m/z=329 (M$^-$–1).

5.3.4.3 Bis(3-Chloro-4-methylphenyl)borinic acid 1-benzyl-4-(hydroxymethyl)imidazole ester (22)

To a solution of 1-benzyl-4-(hydroxymethyl)imidazole (96 mg, 0.521 mmol) in methanol (5 mL), bis(3-chloro-4-methylphenyl)borinic acid (121 mg, 0.521 mmol) was added and the reaction mixture was stirred at room temperature for 2 h. Solvent was removed under reduced pressure and the residue was treated with hexane to give a solid. The product was isolated by filtration and washed with hexane to give product (193 mg, 83%). $^1$H NMR (CDCl$_3$) δ: 2.3 (s, 6H, 2×CH$_3$), 4.8 (brs, 2H, CH$_2$), 5.1 (brs, 2H, CH$_2$), 6.9-7.4 (complex, 13H, Ar—H); MS (ES+) (m/z) 448.78, MF $C_{25}H_{23}BCl_2N_2O$.

5.3.4.4 Bis(3-Chloro-4-methylphenyl)borinic acid-1-methyl-2-(hydroxymethyl)imidazole ester (23)

In a similar manner as in Section 5.3.4.3, the titled compound was obtained from the reaction of bis(3-chloro-4-methylphenyl)borinic acid with 1-methyl-2-(hydroxymethyl) imidazole hydrochloride. The product was obtained as white crystals. MS (ESI+): m/z=373 (M$^+$–1).

5.3.4.5 Bis(3-Chloro-4-methylphenyl)borinic acid 1-ethyl-2-(hydroxymethyl)imidazole ester (24)

In a similar manner as in Section 5.3.4.3, the titled compound was obtained from the reaction of bis(3-chloro-4-methylphenyl)borinic acid with 1-ethyl-2-(hydroxymethyl)imidazole hydrochloride. The product was obtained as white crystals. MS (ESI+): m/z=387 (M$^+$−1).

5.3.4.6 Bis(3-Chloro-4-methylphenyl)borinic acid 1-methyl-4-(hydroxymethyl)imidazole ester (25)

In a similar manner as in Section 5.3.4.3, the titled compound was obtained from the 5 reaction of bis(3-chloro-4-methylphenyl)borinic acid with 1-methyl-4-(hydroxymethyl)imidazole hydrochloride. The product was obtained as white crystals. MS (ESI+): m/z=373 (M$^+$−1).

5.3.4.7 Bis(3-Chloro-4-methylphenyl)borinic acid 2-pyridylethanol (26)

In a similar manner as in Section 5.3.4.3, the titled compound was obtained from the reaction of bis(3-chloro-4-methylphenyl)borinic acid with 2-pyridylethanol. The product was obtained as white crystals. MS (ESI+): m/z=384 (M$^+$−1).

5.3.4.8 Bis(4-Chlorophenyl)borinic acid 2-pyridylmethanol (27)

In a similar manner as in Section 5.3.4.3, the titled compound was obtained from the reaction of bis(4-chlorophenyl)borinic acid with 2-pyridylmethanol. The product was obtained as white crystals. MS (ESI+): m/z=342 (M$^+$−1).

5.3.4.9 Bis(4-Fluorophenyl)borinic Acid 2-pyridylmethanol (28)

In a similar manner as in Section 5.3.4.3, the titled compound was obtained from the reaction of bis(4-fluorophenyl)borinic acid with 2-pyridylmethanol. The product was obtained as white crystals. $^1$H NMR (CDCl$_3$): δ (ppm)=5.3 (s, 2H), 6.9 (t, 4H), 7.3 (t, 4H), 7.5-7.6 (m, 2H), 8.1 (t, 1H), and 8.3 (d, 1H).

In a preferred embodiment, the present invention includes the compounds specifically recited herein, and pharmaceutically acceptable salts thereof, and compositions of any of these compounds where these comprise a pharmaceutically acceptable carrier.

The present invention also relates to a method for treating a microbial-caused disease in a patient afflicted therewith and/or preventing such infection in a patient at risk of becoming infected, comprising administering to said patient a therapeutically effective amount of any of the compounds of the invention, preferably one or more of those listed in Tables 1 to 2. In one aspect, the compounds of the invention have antibacterial (i.e., bactericidal and bacteristatic) and anti-fungal (i.e., fungicidal) activity.

In a preferred embodiment, the microbe is a bacterium, preferably a gram positive bacterium, wherein said gram positive bacterium is a member selected from the group consisting of *Propionibacterium* species, *Staphylococcus* species, *Streptococcus* species, *Bacillus* species, *Mycobacterium* species, *Corynebacterium* species, *Clostridium* species, *Actinomyces* species, *Enterococcus* species, and *Streptomyces* species.

What is claimed:

1. A method for treating a surface condition in an animal, comprising administering to said animal an effective amount of a compound having the structure:

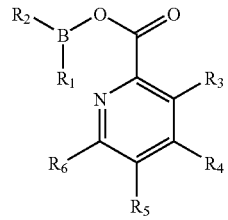

or its pharmaceutically acceptable salts, hydrates, or solvates, wherein:

$R_1$ and $R_2$ are selected independently from the group consisting of optionally substituted alkyl, optionally substituted aryl, aralkyl, and optionally substituted heteroaryl;

$R_3$ and $R_4$ are selected from the group consisting of: hydrogen, alkyl, aryl, aralkyl, heteroaryl, heteroaralkyl, cycloalkyl, heterocyclyl, —COaryl, —OCOalkyl, —OCH$_2$CH$_2$OH, O(CH$_2$)$_3$CO$_2$H, 2-(morpholino)ethoxy, —(CH$_2$)$_k$OH (where k=1, 2 or 3), —CH$_2$NH$_2$, —CH$_2$NHalkyl, —CH$_2$N(alkyl)$_2$, —CO$_2$H, —CO$_2$alkyl, —CONH$_2$, —OH, alkoxy, aryloxy, —SH, —S-alkyl, —S-aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, and —CONHalkyl, wherein $R_3$ and $R_4$ are optionally substituted; and $R_5$ and $R_6$ are selected independently from the group consisting of: hydrogen, alkyl, aryl, aralkyl, heteroaryl, heteroaralkyl, cycloalkyl, heterocyclyl, —(CH$_2$)OH (n=1 to 3), —CH$_2$NH$_2$, —CH$_2$NHalkyl, —CH$_2$N(alkyl)$_2$, halogen, —CHO, —CH=NOH, —CO$_2$H, —CO$_2$-alkyl, —S-alkyl, —SO$_2$-alkyl, —SO-alkyl, —S-aryl, —SO$_2$N(alkyl)$_2$, —SO$_2$NHalkyl, —SO$_2$NH$_2$, amino, alkoxy, —CF$_3$, —SCF$_3$, —NO$_2$, —SO$_3$H, and OH; and wherein said surface condition is selected from the group consisting of acne vulgaris, acne rosacea, atopic dermatitis and periodontal disease.

2. The method of claim 1, wherein one of $R_1$ and $R_2$ is optionally substituted aryl.

3. The method of claim 2, wherein one of $R_1$ and $R_2$ is optionally substituted heteroaryl.

4. The method of claim 3, wherein said optionally substituted heteroaryl is optionally substituted pyridyl.

5. The method of claim 4, wherein one of $R_1$ and $R_2$ is optionally substituted phenyl.

6. The method of claim 5, wherein said optionally substituted phenyl is phenyl substituted by a moiety selected from the group consisting of: hydrogen, alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, —S-alkyl, —S-aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl.

7. The method of claim 2, wherein both $R_1$ and $R_2$ are optionally substituted aryl.

8. The method of claim 7, wherein each of $R_1$ and $R_2$ is optionally substituted phenyl.

9. The method of claim 8, wherein $R_3$ is hydrogen, —OH, alkoxy, or carboxy.

10. The method of claim 9, wherein said optionally substituted phenyl is phenyl substituted by a moiety selected from the group consisting of: hydrogen, alkyl, cycloalkyl, aryl, substituted aryl, aralkyl, —$(CH_2)_k$OH (where k=1, 2 or 3), —$CH_2NH_2$, —$CH_2$NH-alkyl, —$CH_2$N(alkyl)$_2$, —$CO_2$H, —$CO_2$alkyl, —$CONH_2$, —CONHalkyl, —CON(alkyl)$_2$, —OH, alkoxy, aryloxy, —SH, —S-alkyl, —S-aryl, —$SO_2$alkyl, —$SO_2$N(alkyl)$_2$, —$SO_2$NHalkyl, —$SO_2NH_2$, —$SO_3$H, —$SCF_3$, —CN, halogen, —$CF_3$, —$NO_2$, amino, substituted amino, —$NHSO_2$alkyl, —$OCH_2CH_2NH_2$, —$OCH_2CH_2$NHalkyl, —$OCH_2CH_2$N(alkyl)$_2$, oxazolidin-2-yl, and alkyl substituted oxazolidin-2-yl.

11. The method of claim 10, wherein $R_3$ is —OH or carboxy.

12. The method of claim 11, wherein said compound is a member selected from bis(3-chloro-4-methylphenyl)borinic acid 3-hydroxypicolinate ester, bis(2-methyl-4-chlorophenyl)borinic acid 3-hydroxypicolinate ester, (3-chloro-4-methylphenyl)(phenethyl)borinic acid 3-hydroxypicolinate ester, (3-bromo-6-chloro-2-fluorophenyl)(2-fluoro-4-chlorophenyl)borinic acid 3-hydroxypicolinate ester, bis(2-chloro-4-methylphenyl)borinic acid 3-carboxypicolinate ester, (2-methoxy-5-chlorophenyl)(3-chlorophenyl)borinic acid 3-hydroxypicolinate ester and bis(3-chlorophenyl) borinic acid 6-acetylamino-3-hydroxypicolinate ester.

13. The method of claim 11, wherein $R_3$ is —OH.

14. The method of claim 13, wherein said optionally substituted phenyl is phenyl substituted by a moiety selected from the group consisting of: hydrogen, halogen, and alkyl.

15. The method of claim 14, wherein said halogen is chloro.

16. The method of claim 15, wherein said alkyl is methyl.

17. The method of claim 16, wherein said compound is (bis(3-chloro-4-methylphenyl)boryloxy)(3-hydroxypyridin-2-yl)methanone.

18. The method of claim 17, wherein said compound is a solvate of said (bis(3-chloro-4-methylphenyl)boryloxy)(3-hydroxypyridin-2-yl)methanone.

19. The method of claim 17, wherein said compound is a hydrate of said (bis(3-chloro-4-methylphenyl)boryloxy)(3-hydroxypyridin-2-yl)methanone.

20. The method of claim 1, wherein said skin condition is acne vulgaris.

21. The method of claim 1, wherein said skin condition is acne rosacea.

22. The method of claim 1, wherein said skin condition is atopic dermatitis.

23. The method of claim 1, wherein said surface condition occurs in an oral cavity of said animal.

24. The method of claim 1, wherein said surface condition is periodontal disease.

25. The method of claim 17, wherein said surface condition is periodontal disease.

26. The method of claim 1, wherein said surface condition is a surface infection.

27. The method of claim 1, wherein said compound is administered in a dosage of from about 100 to about 2000 mg/day.

28. The method of claim 1, where said animal is a human.

29. A method for treating a surface condition in an animal, comprising administering to said animal an effective amount of (bis(3-chloro-4-methylphenyl)boryloxy)(3-hydroxypyridin-2-yl)methanone, or its pharmaceutically acceptable salts, hydrates, or solvates, wherein said surface condition is periodontal disease.

30. The method of claim 29, wherein said surface condition is a surface infection.

31. The method of claim 29, wherein said (bis(3-chloro-4-methylphenyl)boryloxy)(3-hydroxypyridin-2-yl)methanone is administered in a dosage of from about 100 to about 2000 mg/day.

32. The method of claim 29, wherein said animal is a human.

* * * * *